US012606512B2

(12) United States Patent
Vogelsang et al.

(10) Patent No.: US 12,606,512 B2
(45) Date of Patent: Apr. 21, 2026

(54) PROCESS FOR THE HYDROFORMYLATION OF OLEFINS IN HOMOGENEOUS PHASE

(71) Applicant: OXEA GmbH, Monheim am Rhein (DE)

(72) Inventors: Dennis Vogelsang, Dülmen (DE); Lars Hüttermann, Gelsenkirchen (DE); Tim Wilmsen, Herne (DE)

(73) Assignee: OXEA GmbH (DE)

( * ) Notice: Subject to any disclaimer, the term of this patent is extended or adjusted under 35 U.S.C. 154(b) by 421 days.

(21) Appl. No.: 18/036,457

(22) PCT Filed: Nov. 30, 2021

(86) PCT No.: PCT/EP2021/083488

§ 371 (c)(1),
(2) Date: May 11, 2023

(87) PCT Pub. No.: WO2022/117537

PCT Pub. Date: Jun. 9, 2022

(65) Prior Publication Data

US 2023/0399283 A1 Dec. 14, 2023

(30) Foreign Application Priority Data

Dec. 4, 2020 (EP) .................................... 20211815

(51) Int. Cl.
*C07C 45/50* (2006.01)
*B01J 31/24* (2006.01)
*B01J 35/27* (2024.01)

(52) U.S. Cl.
CPC ........... *C07C 45/50* (2013.01); *B01J 31/2404* (2013.01); *B01J 35/27* (2024.01); *B01J 2231/321* (2013.01); *B01J 2531/004* (2013.01); *B01J 2531/822* (2013.01)

(58) Field of Classification Search
CPC .............................. C07C 45/50; C07C 45/505
See application file for complete search history.

(56) References Cited

U.S. PATENT DOCUMENTS

| | | | |
|---|---|---|---|
| 7,015,362 B2 | 3/2006 | Lappe et al. |
| 7,122,706 B2 | 10/2006 | Lappe et al. |
| 7,193,116 B2 | 3/2007 | Möeller et al. |
| 2017/0179323 A1 | 6/2017 | Hishida et al. |

FOREIGN PATENT DOCUMENTS

| | | | | |
|---|---|---|---|---|
| CN | 1149043 | A | | 5/1997 |
| CN | 1227214 | A | | 9/1999 |
| CN | 1556079 | A | * | 12/2004 |
| DE | 19532393 | A1 | | 3/1997 |
| DE | 69823463 | T2 | | 4/2005 |
| DE | 102006004318 | A1 | | 8/2007 |
| EP | 1529769 | A1 | | 5/2005 |
| EP | 1529771 | A1 | | 5/2005 |
| JP | 1997-124534 | A | | 5/1997 |
| JP | 2005139179 | A | | 6/2005 |
| JP | 2005139181 | A | | 6/2005 |
| JP | 2007-204470 | A | | 8/2007 |
| WO | 2004024661 | A1 | | 3/2004 |

OTHER PUBLICATIONS

Mercer, S. M. et al. "Recycling of a homogeneous catalyst using switchable water" Catal. Sci. Technol., 2012, 2, 1315-1318 and Supporting information pp. 1-20 (Year: 2012).*

Jingchang (Jingchang, Z. et al. "Hydroformylation of propylene in supercritical CO2+H2O and supercritical propylene +H2O" Journal of Molecular Catalysis A: Chemical 260 (2006) 95-99) (Year: 2006).*

Human Metabolome Database "Showing metabocard for 2-Methylpropan-2-ol (HMDB0031456)" Sep. 11, 2012 (Year: 2012).*

Machine translation of CN1556079A, Dec. 22, 2004, pp. 1-21 (Year: 2004).*

Sigma-Aldrich ("1,4-Pentadiene" Deposit and available date Jul. 16, 2007 (Year: 2007).*

* cited by examiner

*Primary Examiner* — Medhanit W Bahta

(74) *Attorney, Agent, or Firm* — M. Susan Spiering; Ochow & Associates, P.C

(57) ABSTRACT

The present invention relates to a process for the preparation of aldehydes by hydroformylation of olefins by means of synthesis gas over a transition metal complex catalyst, wherein within a first process step the olefins are reacted by means of a water-soluble transition metal complex catalyst consisting of a metal and ligands bound thereto in the presence of a water-miscible solvent, the pressure, temperature and proportions of the solvent and aqueous catalyst solution being controlled so that the hydroformylation is carried out in a homogeneous single-phase reaction solution and within a second process step, by lowering the temperature and/or reducing the pressure, the homogeneous reaction solution obtained from the first reaction step is converted into a two-phase process solution and at least part of the organic phase is separated from the aqueous phase.

14 Claims, 1 Drawing Sheet

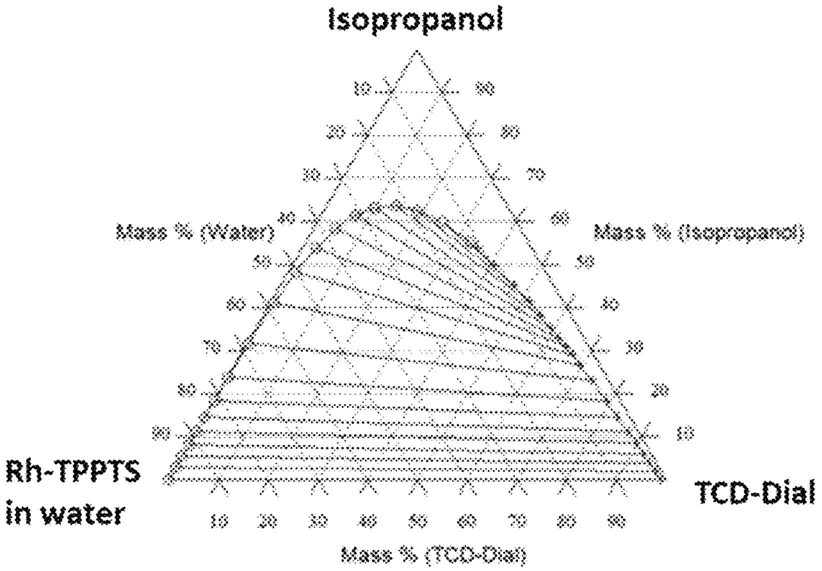
Isopropanol
Mass % (Water)
Mass % (Isopropanol)
Rh-TPPTS in water
TCD-Dial
Mass % (TCD-Dial)
10
20
30
40
50
60
70
80
90

PROCESS FOR THE HYDROFORMYLATION OF OLEFINS IN HOMOGENEOUS PHASE

CLAIM FOR PRIORITY

This application is a national phase application based on Application Number PCT/EP2021/083488. Application No. PCT/EP2021/083488, filed Nov. 30, 2021 was based on Application No. EP 20211815.4, filed Dec. 4, 2020. The priorities of the foregoing applications is hereby claimed and their disclosures incorporated herein by reference.

TECHNICAL FIELD

The present invention relates to a process for the preparation of aldehydes by hydroformylation of olefins by means of synthesis gas over a transition metal complex catalyst, wherein within a first process step the olefins are reacted by means of a water-soluble transition metal complex catalyst consisting of a metal and ligands bound thereto in the presence of a water-miscible solvent, the pressure, temperature and proportions of the solvent and aqueous catalyst solution being controlled so that the hydroformylation is carried out in a homogeneous single-phase reaction solution and within a second process step, by lowering the temperature and/or reducing the pressure, the homogeneous reaction solution obtained from the first reaction step is converted into a two-phase process solution and at least part of the organic phase is separated from the aqueous phase.

BACKGROUND

The further functionalization of olefins by hydroformylation with synthesis gas in the presence of a metal catalyst has been known for a long time. As primary products of the reaction, aldehydes with one more carbon atom than the reactant olefin are obtained. These aldehydes can be used as such, or preferably themselves as further reactants, to produce a variety of useful downstream products. Important industrial downstream products of the actual hydroformylation are alcohols obtainable from the aldehydes, for example by hydrogenation, such as butanol or 2-ethylhexanol, which can be obtained via the aldehydic intermediate from propene as the olefin starting material. The final products of the hydroformylation are used in a variety of ways as solvents, as intermediates for the production of detergents and cleaning agents, lubricants or plasticizers for plastics.

While the basic interrelationships of the conversion of olefins to aldehydes are well known, a large number of optimization approaches still arise in large-scale processes, since the economic efficiency of the overall process is characterized by a complex interplay of reaction conditions, reactant conversion, desired selectivity, and catalyst lifetimes and recovery. In particular, the catalysts and their efficient use are of outstanding importance in this matrix, since the costs of the metals usually used far exceed those of the other reaction participants.

This has led to the development of a large number of different large-scale process options, the various process designs of which can be found in numerous documents in the patent literature.

For example, WO 2004 024 661 A1 discloses a process for the catalytic hydroformylation of olefinically unsaturated compounds having 3 to 24 carbon atoms, wherein at least one unmodified catalyst containing a metal of the 8th to 10th group of the Periodic Table of the Elements is used as the catalyst, wherein the hydroformylation is carried out in the presence of a cyclic carbonic ester of the following formula

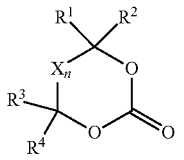

$R^1$, $R^2$, $R^3$, $R^4$: are each the same or different: H, substituted or unsubstituted, aliphatic, alicyclic, aromatic, aliphatic-alicyclic, aliphatic-aromatic, alicyclic-aromatic hydrocarbon radicals having 1 to 27 carbon atoms.

n: 0-5

X: divalent substituted or unsubstituted, aliphatic, alicyclic, aromatic, aliphatic-alicyclic, aliphatic-aromatic hydrocarbon radical having 1 to 27 carbon atoms.

is carried out, the proportion of the carbonic acid ester being at least 1% by weight of the reaction mixture.

In another patent document, EP 1 529 771 A1, a process for the preparation of 8(9)-formyl-tricyclo[5.2.1.0 26]dec-3-ene by hydroformylation of dicyclopentadiene in a heterogeneous reaction system using an aqueous solution is disclosed, wherein water-soluble organic phosphorus(III) compounds in complex bonding containing transition metal compounds of Group VIII of the Periodic Table of the Elements are reacted with synthesis gas at temperatures of 70 to 150° C. and pressures of 0.5 to 10 MPa, special sulfonated triarylphosphines being used as water-soluble organic phosphorus(III) compounds.

Another possibility for the reaction of cyclic compounds with multiple double bonds is disclosed in DE 10 2006 004 318 A1. This describes a process for the preparation of 3(4),7(8)-dihydroxymethyl-bicyclo[4.3.0]nonane by hydroformylation of bicyclo[4.3.0]nona-3,7-diene with subsequent hydrogenation, wherein bicyclo[4.3.0]nona-3,7-diene is reacted with synthesis gas in homogeneous organic phase in the presence of transition metal compounds of Group VIII of the Periodic Table of the Elements containing organophosphorus compounds in complex bonding and excess organophosphorus compound at temperatures of 70 to 160° C. and pressures of 5 to 35 MPa, and the 3(4),7(8)-bisformyl-bicyclo[4.3.0]nonane is then hydrogenated to give the 3(4),7(8)-dihydroxymethyl-bicyclo[4.3.0]nonane.

Such solutions known from the prior art may offer further potential for improvement, in particular with respect to the possible efficiency of the conversion, the simplicity of the separation of the reaction mixture, and the possibility of reusing the catalyst material employed.

SUMMARY OF INVENTION

It is therefore the object of the present invention to at least partially overcome the disadvantages known from the prior art. In particular, it is the task of the present invention to provide a process which enables an efficient conversion of olefins which are difficult to hydroformylate and, furthermore, a simple and efficient separation of the reaction solution with improved reuse of the catalyst.

The problem is solved by the features of the independent process claim. Preferred embodiments of the invention are indicated in the dependant claims, in the description or in the figures, whereby further features described or shown in the dependant claims or in the description or in the figures may individually or in any combination constitute an object of the invention, unless the opposite clearly follows from the context.

According to the invention, the problem is solved by a process for the preparation of aldehydes by hydroformylation of olefins by means of synthesis gas on a transition metal complex catalyst, wherein within a first process step the olefins are reacted by means of a water-soluble transition metal complex catalyst consisting of a metal and ligands bound thereto in the presence of a water-miscible solvent, the pressure, temperature and proportions of the solvent and aqueous catalyst solution being controlled so that the hydroformylation is carried out in a homogeneous single-phase reaction solution and within a second process step, by lowering the temperature and/or reducing the pressure, the homogeneous reaction solution obtained from the first reaction step is converted into a two-phase process solution and at least a part of the organic phase is separated from the aqueous phase.

Surprisingly, it was found that a large number of different olefins can be highly selectively converted to the corresponding aldehydes using the process according to the invention in the controlled single-phase reaction environment with aqueous catalyst component, whereby high conversions are achieved within short process times even when difficult-to-react olefin starting materials with one or more double bonds and/or one or more ring structures are used. In addition to the very efficient conversion within the reaction environment, the controlled composition of the reaction environment also facilitates the work-up of the reaction solution after the end of the reaction to a considerable extent. A further advantage is that the desired organic products and the catalyst solution can be separated easily and thermally gently, which allows the cost-intensive catalyst to be easily reprocessed and reused without significant losses in reactivity and material. Without being bound by theory, the single-phase reaction environment appears to protect the catalyst, or more specifically the organic ligands of the catalyst complex, from premature degradation under the given reaction conditions. Furthermore, the controlled transfer of the reaction solution into a two-phase system of organic product and aqueous catalyst phase in the second process step seems to prevent a significant loss of catalyst system in the work-up, with both the recoverable amount and the activity of the catalyst being higher compared to other catalyst work-up processes. This is especially true when compared to reactions in purely organic phase, which show difficulty in recovering the non-water soluble catalyst. The water-soluble catalysts are separated from the organic product phase after the reaction by mechanical separation of the aqueous catalyst phase. Thus, the water-soluble catalyst system is not thermally stressed, in contrast to the distillative separations for reactions in purely organic phase. A high and continuous thermal load on the catalyst often leads to its deactivation. In this respect, the coupling of the two process steps according to the invention results in a synergistic effect, which promotes highly efficient and catalyst-protecting conversions in the large-scale industrial environment.

The process according to the invention is a process for the preparation of aldehydes by hydroformylation of olefins by means of synthesis gas over a transition metal complex catalyst. The starting materials may be olefins or mixtures of olefins having from 4 to 24 carbon atoms, preferably having from 6 to 20 carbon atoms and more preferably having from 8 to 20 carbon atoms. The mixtures may comprise olefins having one or more terminal and/or internal C—C double bonds. The mixtures may comprise or consist of olefins having the same, similar (±2) or significantly different (>±2) carbon atom number (C number). They may be straight chain, branched or cyclic olefins. The olefins may be aliphatic olefins having none, one or more ring structures. Thus, the olefins may have one, two, three or more rings in the molecule, and the double bonds may be present in or on the ring structures. Typically, these olefins are incompletely reacted in conventional hydroformylation processes. An aldehyde (HC═O) is obtained from these olefins by reaction with synthesis gas, i.e. hydrogen and carbon monoxide, the C-number of the olefin being increased by 1 by the reaction.

In the hydroformylation step of the first process step, preferably a synthesis gas of carbon monoxide and hydrogen is used in which the molar ratio of carbon monoxide to hydrogen is preferably from 1:4 to 4:1, more preferably from 1:2 to 2:1, most preferably from 1:1.2 to 1.2:1. In particular, a synthesis gas can be used in which an approximately stoichiometric ratio of carbon monoxide to hydrogen is present.

Within the first process step, the olefins are reacted using a water-soluble transition metal complex catalyst comprising a metal and ligands bonded thereto. Applicable hydroformylation catalysts comprise a metal and one or more ligands coordinated to the metal. As such, the catalysts may be added preformed to the reaction environment or the active catalyst may form in situ under the reaction conditions from another metal source, such as a metal salt, in the reaction zone. The latter, for example, by addition or exchange of ligands present in the reaction zone, such as CO, hydrogen or organic complex ligands. Preferably, the transition metal complex catalyst may be a metal of the 8th-10th subgroup of the periodic table and in particular Co, Ru, Rh, Pd, Pt, Os or Ir, more particularly Rh, Co, Ir or Ru. The water solubility of the catalyst complex is thereby essentially co-determined by the choice of ligands, the catalyst being water soluble according to the invention if the solubility of the catalyst in water at 20° C. is greater than or equal to 100 g/L. The solubility can be determined, for example, according to an OECD method ("OECD Guideline For The Testing Of Chemicals", "Water solubility" of 27.07.1995). The ligands may be inorganic counterions such as halogens or more complex organic molecules such as acetates or aromatic complex ligands containing one or more heteroatoms.

In the first stage of the process, the reactants are reacted in the presence of a water-miscible solvent. The hydroformylation of the olefin via the addition of synthesis gas to the aldehydes takes place in the presence of a further solvent which is not water. Preferred solvents may be liquids which have at least some solubility with water. This solubility of the solvent in water may be greater than or equal to 20 g/L at 20° C., for example. Suitable solvents in this group may be, for example, lower monoalcohols or diols. The solvent may also preferably be completely miscible with water. The use of solvents in this solubility ratio to water can help to obtain particularly robust single-phase regions, which can also reliably compensate for pressure and/or temperature fluctuations that may occur. In addition, the use of such a group of solvents may help to compensate for large changes in composition due to the formation of products. Furthermore, the proportion of solvents can be kept sufficiently small, which facilitates the separation of the resulting mixture and keeps energy costs for separation low.

The pressure, the temperature and the proportions of the solvent and the aqueous catalyst solution are controlled in the first process step so that the hydroformylation is carried out in a homogeneous single-phase reaction solution. Due to the presence of an aqueous catalyst solution, non-water-soluble olefinic reactants and only slightly water-soluble aldehydic products, a two-phase solution is formed in the reaction zone under the reaction conditions without further measures, which is opposed to an efficient conversion of the reactants. With the addition of the further solvent, either single-phase or two-phase regions can exist in the phase diagram, depending on the amount of aqueous catalyst—amount of solvent—amount of reactant or amount of product/intermediate, under the reaction conditions. The change between the single-phase or two-phase region can be controlled by the use of the amounts of, in particular, the amount of aqueous catalyst and the amount of solvent such that the reaction always proceeds in the single-phase region under the given pressure and temperature conditions. By using the correct ratio of amounts of aqueous catalyst solution and solvent, together with the correct solubility or miscibility of the solvent with water, the reaction can be run in the single-phase range, even with changing or increasing proportions of intermediate as well as final products. Control can be achieved, for example, by specifying the required ratio of solvent to aqueous catalyst solution at the start of the reaction. However, it is also possible to adjust the quantities of one or the other component during the course of the reaction, so that the phase diagram is always run in the single-phase region. The latter mode of operation can be effected, for example, by a controlled addition of solvent into the reaction zone, which is adapted, for example, to the quantity of the products formed. The basic single-phase or two-phase phase ranges of the phase diagram can be found in the literature, calculated (see FIG. 1) or determined with reasonable effort by orienting experiments with changing compositions of selected catalyst in aqueous solution, solvent and reactant/product under reaction conditions.

Within a second process step, by lowering the temperature and/or reducing the pressure, the homogeneous reaction solution obtained from the first reaction step is converted into a two-phase process solution and at least part of the organic phase is separated from the aqueous phase. From the possible set of single-phase compositions of aqueous catalyst solution, solvent and olefinic reactant/product, under the chosen reaction conditions, it is possible to determine, by simple orientating experiments, the subset of possible compositions which lead to a change in the phase range due to the change in temperature and/or pressure. These compositions are then suitable and capable of falling into the two-phase state at the end of the reaction by a simple change in the reaction conditions, thus bringing about a simple separation between the organic and aqueous phases. This portion of the single-phase region is generally closer to the phase boundary line between the single-phase and two-phase regions, and the phase separation as a function of pressure and/or temperature conditions can be followed purely visually, for example. The separation of the two phases may be carried out, for example, via purely mechanical steps such as decantation. However, it is also possible that the two phases are separated from each other without mechanical, purely via thermal separation methods. Due to the two-phase nature of the reaction solution, thermal separation operations can also be carried out in a simpler and more resource-efficient manner. Of course, for work-up purposes, it is also possible to couple mechanical separation operations with thermal separation operations, whereby the thermal load on the catalyst system is low due to the low boiling point of the selected solvent in the process according to the invention.

Further details are provided in the following description and accompanying drawing.

BRIEF DESCRIPTION OF DRAWING

FIG. 1 shows the result of the calculated phase behaviour of a three-component mixture as a function of the composition at a temperature of 120° C. The components are the aqueous solution of a Rh-TPPTS complex catalyst (bottom left), isopropanol as solvent (top) and the final product TCD dial (bottom right).

DETAILED DESCRIPTION

In a preferred embodiment of the process, the temperature and the pressure can be kept constant during the reaction and the single phase of the reaction solution can be adjusted via the mass ratios of solvent to aqueous catalyst solution. It has also been found to be advantageous for efficient process control that the desired single-phase phase range during the reaction is essentially adjusted via the mass ratios of aqueous catalyst solution to solvent. "Safe" phase ranges can be set here, so that the change in composition in the course of the reaction due to the formation of the intermediate and/or end products and also the formation of higher molecular weight by-products can be reliably compensated. In addition, the choice of suitable solvents and their quantity in relation to the aqueous catalyst solution can also be used to compensate for any temperature and/or pressure fluctuations that may occur during the reaction. Via this determination, the reaction in its entirety can be reliably maintained in the single-phase range. Further preferably, this control can be determined by the choice of the amounts of solvent and aqueous catalyst solution at the beginning of the reaction.

In a preferred embodiment of the method, the first process step may be performed at a pressure of greater than or equal to 0.5 MPa and less than or equal to 10 MPa and at a temperature of greater than or equal to 70° C. and less than or equal to 150° C. Due to the increased reactivity with the synthesis gas by driving in the single-phase range, the above temperature interval has been found to be particularly advantageous. In this range, particularly fast and selective conversions are obtained, whereby in particular the proportion of high boilers formed can be kept very low. In addition, catalyst lifetimes are significantly prolonged, which can probably be attributed to reduced degradation of the ligands in the reaction solution. Surprisingly, it has also been shown that within this temperature range, particularly low pressures are also sufficient for the conversion of difficult reactants. This is especially true for sterically challenging reactants or double reactions when diolefin reactants are used. Even in these reactions, the aqueous component in the single-phase region does not appear to inhibit the entry of the synthesis gas, so that overall even lower pressures can ensure sufficient gas entry into the reaction solution.

Within a further preferred aspect of the process, the olefins may have at least two non-conjugated double bonds. The process according to the invention is particularly suitable for the reaction of challenging reactants which may, for example, have two or more isolated double bonds. It has been shown that the reaction of even two double bonds within a single-phase reaction is possible. This is surprising, since reactions carried out in the two-phase range usually only allow the conversion of one double bond. In addition, compared to two-phase reactions, single-phase reactions can be faster, more selective and form a lower proportion of high-boiling by-products. The double bonds of the dienes may be present within aliphatic chains and/or cycles. Preferably, short or medium chain aliphatic di- or higher olefins may be reacted. Thus, it is possible to react olefins having two or more unsaturated bonds with a molecular weight greater than or equal to 50 g/mol and less than or equal to 500 g/mol.

Within the scope of a preferred characteristic of the process, the olefins may have at least one aliphatic ring. It has also been found to be particularly advantageous that olefin starting materials which are sterically difficult to react and which have a rigid aliphatic ring structure can also be reacted within the single-phase process according to the invention. Typically, these olefins react much more poorly with the catalysts compared to short aliphatic chains in solution or, in the case of multiple double bonds, stop at the stage of an intermediate. The reactants can be mono- or polycyclic. Single-phase reactions in pure organic solvents and in pure organic phase are possible, but lead to increased problems in the purification of the products obtained. Furthermore, the latter reactions show problems in the catalyst recovery as well as its lifetime. For example, in reactions in purely organic solvents, unmodified (without addition of ligands) metal catalysts are also used for the reaction of the diolefins mentioned here, for which high amounts of catalyst are required and the catalyst is not recycled. When ligand-metal complexes are used as catalysts, the desired activities are often not achieved for the hydroformylation of the polycyclic diolefins. The mono- bi- or tri-cyclic olefins comprise two or three closed, non-aromatic rings and may further preferably have a molecular weight greater than or equal to 60 g/mol and less than or equal to 450 g/mol.

In a further preferred embodiment of the process, the molar ratio of water in the aqueous catalyst solution used to catalyst metal, expressed as moles of water divided by moles of catalyst metal, may be greater than or equal to 5000 and less than or equal to 60000. Despite the fact that the access of the organic reactants to the catalyst should be improved by a more organic environment, the ratio of water to catalyst given above has been found to be particularly favourable. With these proportions of water, complete conversions to the dialdehydes are also achieved for diene reactants and the process control can also be safely designed as a single phase. In addition, fluctuations in the reaction conditions can be safely compensated without leaving the single-phase phase region. Moreover, this water-catalyst metal ratio also appears to be suitable for enabling safe and complete separation of the aqueous catalyst phase in the second process step. Due to these water proportions, the catalyst and its ligands are both sufficiently protected in the single-phase reaction. Moreover, even after changing the reaction conditions and decomposition of the single-phase reaction into a two-phase reaction, a sufficient aqueous environment can be maintained, which promotes the reusability of the catalyst solution.

According to a further preferred embodiment of the process, the metal of the water-soluble transition metal complex catalyst may be rhodium and the ligands comprise water-soluble diphosphines or triarylphosphines. The catalyst employed or the catalyst system forming in the reaction solution comprises the transition metal rhodium. This metal can allow particularly fast reaction kinetics in single-phase solutions and can also safely convert sterically difficult polyenes or olefins with rigid ring structures. In addition to the metal, the catalyst has at least one diphosphine ligand with two phosphorus atoms or one or more organic triarylphosphine ligands with one phosphorus atom in its coordination sphere or coordinates them in the reaction solution under the reaction conditions. The catalytically active system is further formed under the reaction conditions by further addition of hydrogen and carbon monoxide in the reaction solution, the components of the synthesis gas forming a coordinative complex with the metal. However, it is also possible to first preform the catalyst and then feed it to the actual hydroformylation stage. In this case, the preforming conditions generally correspond to the hydroformylation conditions.

For example, the triarylphosphines may have the general formula

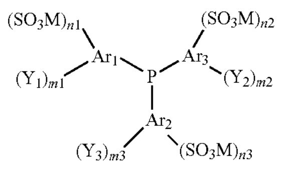

correspond to. In this formula, $Ar_1$, $Ar_2$ and $Ar_3$ represent the same or different aryl groups having 6 to 14 carbon atoms. The substituents $Y_1$, $Y_2$ and $Y_3$ represent identical or different straight-chain or branched alkyl or alkoxy groups having 1 to 4 carbon atoms, chlorine, bromine, hydroxyl, cyanide or nitro groups, and furthermore amino groups of the formula $NR^1R^2$, where the substituents Wand R 2 may be identical or different and represent hydrogen, straight-chain or branched alkyl groups having 1 to 4 carbon atoms. The countercations M may represent lithium, sodium, potassium, magnesium, calcium or barium, where m1, m2 and m3 may be identical or different and represent integers from 0 to 5, in which n1, n2 and n3 are identical or different and represent integers from 0 to 3, at least one of the numbers n1, n2 and n3 being equal to or greater than 1. A triarylphosphine complex catalyst is a water-soluble triarylphosphine complex catalyst when the solubility of the complex in water at 20° C. is greater than or equal to 100 g/L.

The water-soluble triarylphosphines of the above formula preferably include those triarylphosphines in which the groups $Ar_1$, $Ar_2$, $Ar_3$ are phenyl groups; $Y_1$, $Y_2$ and $Y_3$ represent a methyl group, an ethyl group, a methoxy group, an ethoxy group and/or a chlorine atom. The cationic moieties M of the inorganic cations may preferably be sodium, potassium, calcium and barium. In particular, suitable water-soluble triarylphosphines may be those in which $Ar_1$, $Ar_2$, $Ar_3$ each represent a phenyl group; m1, m2, m3 are 0, n1, n2 and n3 are 0 or 1 and n1+n2+n3 together account for 1 to 3, wherein the sulfonate groups may preferably be in the meta position. The ligands may be used as such or as mixtures. Suitable examples of water-soluble triarylphosphine ligands include (sulfophenyl)-diphenylphosphine, di-(sulfophenyl)phenylphosphine and tri(sulfophenylphosphine). In the prior art, (sulfophenyl)diphenylphosphine is abbreviated as TPPMS, di-(sulfophenyl)phenylphosphine is abbreviated as TPPDS, and tri(sulfophenyl)phosphine is abbreviated as TPPTS. These ligands can contribute to sufficient water solubility of the catalyst complex and are stable in both the single-phase and two-phase regimes.

Sulfonated diphosphines of the general formulae (III) and (IV) are also suitable as water-soluble diphosphines.

(III)

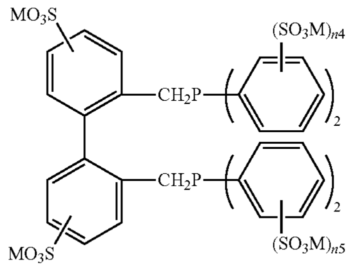

(IV)

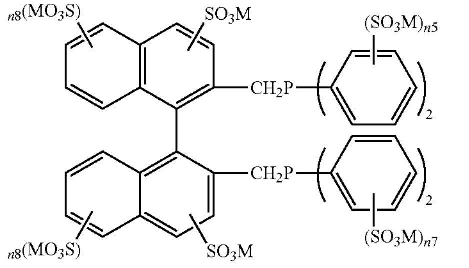

In (III), each n4 and n5 independently represents 0 or 1, and the compound of formula (III) may contain up to six $—SO_3M$ groups.

In (IV), each n6, n7, n8 and n9 independently represents 0 or 1, wherein the compound of formula (IV) contains from four to eight $—SO_3M$ groups.

In formulae (III) and (IV), M represents ammonium, a monovalent metal or the equivalent of a polyvalent metal, in particular sodium, potassium, calcium or barium.

In a preferred embodiment of the process, the mass ratio of aqueous catalyst solution to solvent, expressed as mass of catalyst solution divided by mass of solvent, may be greater than or equal to 0.25 and less than or equal to 4. In the single-phase reaction solution, the above mass ratio has been found to be particularly safe and advantageous. This mass ratio can also be used to reliably compensate for unavoidable fluctuations in pressure and temperature due to the process, and for changes in composition due to the formation of the products. Further advantageously, a relatively small amount of solvent additive of greater than or equal to 0.5 and less than or equal to 2, in particular preferably of greater than or equal to 0.75 and less than or equal to 1.5, can be obtained relative to the mass of the catalyst solution. This low solvent addition can contribute to a more efficient work-up of the reaction solution after the end of the reaction.

In a further preferred aspect of the method, the water miscible solvent may have a solubility in water at 20° C. greater than or equal to 20 g/L. Thus, in order to obtain the most stable single-phase range with the least amount of solvent addition, it has been found particularly suitable for the solvent to have a miscibility with water within the range indicated above. Such single-phase reaction solutions can be stable with respect to the changes in the reaction environment caused by the added products and also with respect to possible changes in the reaction parameters of pressure and temperature, and can also provide a particularly favourable phase separation of the organic and aqueous phases after the end of the reaction. In particular, the proportion of recoverable catalyst after the end of the reaction may be increased by this group of solvents. In a further preferred embodiment, the solubility of the solvent may be greater than or equal to 60 g/I, further preferably greater than or equal to 70 g/I, and further preferably greater than or equal to 80 g/I at 20° C. In a further preferred embodiment, the solvent may be completely miscible with water at 20° C.

In a preferred characteristic of the process, the solvent may be selected from the group consisting of straight-chain or branched C2-C5 alcohols or mixtures of at least two alcohols from this group. In particular, the short-chain alcohols have been found to be especially suitable for obtaining particularly efficient conversions in a single-phase region. By means of these solvents, reactants which are difficult to hydroformylate can also be highly selectively reacted within very short process times on water-soluble catalysts. The service life of the catalysts can also be significantly extended by this choice of solvent. These solvents show a low binding affinity to the metal compared to the ligand. At the same time, however, they can have a stabilizing effect on the ligand and thus protect it from degradation. A further advantage results from the fact that very robust single-phase regions can be achieved with only a small mass fraction of solvent, which reduces the costs of working up and separating the desired products. In addition, the solvent selection can help to ensure that the change of the system from single- to two-phase in the second process step is very fast and complete, so that a large part of the catalyst can be recovered and, if necessary, recycled back into the reaction cycle. Furthermore, the low boiling points of the selected solvents are advantageous, allowing them to be easily separated from the product or catalyst system if required.

In a further preferred aspect of the process, the solvent may be isopropanol. The use of isopropanol for the single-phase conversion of olefins in a hydroformylation process has been found to be particularly favorable. By adding isopropanol, olefin products that are difficult to hydroformylate can also be highly selectively converted within very short process times on water-soluble catalysts. The service life of the catalysts can also be significantly extended by this solvent. A further advantage results from the fact that very robust single-phase regions are formed with only a small amount of isopropanol, which reduces the costs of working up and separating the desired products. In addition, due to the physical differences of the isopropanol to the aldehyde products, a particularly simple and complete separation after the end of the reaction can be achieved. In particular, this can also prolong the recyclability of the catalysts.

Within a further preferred embodiment of the process, at least one ligand of the water-soluble transition metal complex catalyst may comprise a triphenylphosphine-3,3',3"-trisulfonic acid sodium salt. The use of these triphenylphosphine ligands has been found to be particularly advantageous for working in the single-phase region. In addition to a highly selective conversion of the olefins used, particularly low amounts of high boilers are formed, even with long reaction times. This results in particular from the use of isopropanol as solvent, whereby in these cases a particularly low degradation of the organic ligand occurs. In addition, catalyst complexes with these ligands can be recycled particularly efficiently from the reaction mixture, for example by recycling them back into the reaction cycle in a continuous reaction. Moreover, the degradation of these ligands appears to be particularly low in the single-phase reaction environment. In a further preferred embodiment, the triphenylphosphine-3,3',3"-trisulfonic acid sodium salt may be the sole aromatic complex ligand of the reaction.

In a further preferred embodiment of the process, the water-soluble transition metal complex catalyst may comprise triarylphosphine ligands and a catalyst metal, wherein the molar usage ratio of triarylphosphine ligands to catalyst metal, expressed as moles of triarylphosphine ligands divided by moles of catalyst metal, is greater than or equal to 3 and less than or equal to 15. For the reactions in the single-phase range, it has been found to be advantageous to keep the ratio of organic ligands to catalyst metal within a narrow range. Within these ratios, very reproducible conversions with high selectivities result. This is probably because a lower ligand concentration allows higher activities of the catalyst. At the same time, the degradation of the organic ligand in the single-phase solution can be delayed or even completely prevented. Thus, this process control can contribute to the catalyst being used more frequently and for a longer period of time. This ratio also makes a greater contribution to protecting the catalyst even during workup, resulting in improved recoverability of the catalyst after separation of the reaction products. Further preferably, the ratio may be greater than or equal to 5 and less than or equal to 12 and more preferably greater than or equal to 7 and less than or equal to 10.

In a further preferred embodiment of the process, the molar ratio of catalyst metal to olefin, expressed as moles of catalyst metal divided by moles of olefin, may be greater than or equal to 0.05% and less than or equal to 0.75%. Single-phase reaction control can also be used very efficiently with a particularly low catalyst to olefin feedstock ratio. Complete conversions to the dialdehydes are achieved within short reaction times, and catalyst lifetimes may also be longer compared to the state-of-the art solutions. The ratio may further preferably be greater than or equal to 0.15% and less than or equal to 0.65%, more preferably greater than or equal to 0.3% and less than or equal to 0.5%.

Within a preferred embodiment of the process, in the second process step, the homogeneous reaction solution obtained from the first reaction step can be converted into a two-phase process solution by lowering the temperature and the product aldehyde can be separated. In the second process step of the process according to the invention, after the conversion of the olefin to the aldehyde, the reaction pressure and/or the reaction temperature can in principle be reduced. This forces the separation of the homogeneous reaction solution obtained in the first reaction step into a two-phase system. One phase contains the aqueous catalyst, whereas the second phase contains the product aldehyde. In particular, the separation of the two phases mainly by temperature allows a gentle mechanical separation of the product from the catalyst. For this purpose, the pressure is significantly changed only after the temperature has been changed by at least 50° C. from the temperature of the reaction zone. A significant change in the reaction pressure occurs when there is a deviation of at least 10% relative to the reaction pressure. It is particularly advantageous that no purely thermal separation is carried out in the form of a distillation, in which higher boilers can preferably be formed and the catalyst system can be deactivated. This is a process method which is carried out under mild conditions.

Within a further embodiment of the process, the pH of the aqueous catalyst solution may be greater than or equal to pH 4 and less than or equal to pH 10. It has been found that by adjusting the pH in the preferred range, the catalyst comprising the transition metal and the water-soluble organophosphorus ligand has very high activity and high selectivity with respect to product formation. The adjustment can be carried out by known adjusting agents such as inorganic acids or bases on the catalyst solution used. However, it is also possible and advantageous that the homogeneous phase forming by means of the aqueous catalyst solution used is maintained at the pH range described. Furthermore, low decomposition of the catalyst has been observed with the preferred pH adjustment. In a further preferred embodiment, the pH can be adjusted between greater than or equal to pH 5 and less than or equal to pH 8, further preferably between greater than or equal to pH 5.5 and less than or equal to pH 7.

In a preferred embodiment of the process, the olefin used may be a polycyclic aliphatic diolefin selected from the group consisting of bi- or tri-cyclic dienes or mixtures thereof. It has been found to be particularly advantageous that sterically difficult cyclic diene reactants with internal double bonds, which react significantly worse in solution with the catalyst complexes due to their rigid ring structure compared to, for example, short aliphatic chains, can be reacted within the process according to the invention. The polycyclic, olefinic aliphatics can only be very incompletely reacted in two-phase regions by conventional process routes. Single-phase reactions in purely organic solvents are possible, but lead to increased problems in the purification of the products obtained. Furthermore, the latter reactions show problems in the catalyst recovery as well as its lifetime. For example, in reactions in purely organic solvents, unmodified (without addition of ligands) metal catalysts are also used for the reaction of the diolefins mentioned herein, for which a high catalyst input is required and the catalyst is not recycled. Using ligand-metal complexes as catalysts, the desired activities are often not achieved for the hydroformylation of the polycyclic diolefins. The bi- or tri-cyclic dienes which can be reacted according to the invention comprise two or three closed, non-aromatic rings and may further preferably have a molecular weight of greater than or equal to g/mol and less than or equal to 450 g/mol.

In a further preferred embodiment of the process, the olefin may be a cyclic aliphatic diolefin selected from the group consisting of dicyclopentadiene or norbornadiene. By means of the reaction according to the invention, in particular sterically difficult to react and poorly water-soluble polycyclic aliphatic olefins such as tricyclo[5.2.1.02,6]deca-3,8-diene and bicyclo[2.2.1]hepta-2,5-diene can be reacted particularly efficiently. High conversions at high selectivities are achieved, and the catalyst system can also exhibit a particularly long service life and improved recoverability.

EXAMPLES

In a hydroformylation according to the invention, dicyclopentadiene DCDP is converted to the corresponding dialdehyde by means of an organically modified rhodium complex catalyst in a homogeneous reaction solution according to the following reaction equation:

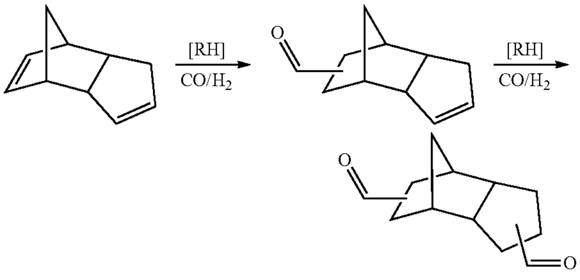

The catalyst used is a water-soluble complex catalyst comprising TPPTS organophosphorus ligands according to the following formula:

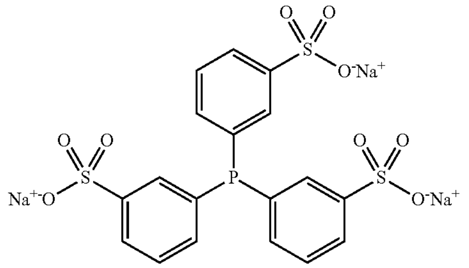

Isopropanol is used as solvent to achieve the single phase of the reaction system. The reaction is carried out at 130° C. and a pressure of 5 MPa in a stirred reactor vessel (800 rpm) within a reaction time of 3 h.

The input quantities of the reactants are as follows:

| Component | Application quantity |
|---|---|
| Total rhodium concentration in aqueous catalyst solution | 46380 mg/l |
| Amount of aqueous catalyst solution | 2.32 ml |
| Rhodium in mol | 1.04 mmol |
| Ligand in g | 18.38 g |
| Ligand in mol | 568 mmol |
| P/Rh ratio | 10:1 |
| Olefin in % based on total input | 10% |
| Olefin in g | 30.0 g |
| olefin in mol | 0.227 mol |
| Rhodium quantity based on olefin | 0.46% |
| Application quantity Isopropanol | 135 g |
| Application quantity water | 135 g |
| Synthesis gas composition $H_2$:CO | 1:1 |

An aqueous catalyst solution of rhodium and the ligand was prepared. Rh(OAc) 2 was used as the rhodium source. This solution was added to the reactor with the above amount of isopropanol. Dicyclopentadiene was added and allowed to react at 5 MPa synthesis gas pressure and 130° C. for 3 h. The reaction was stopped. After cooling and depressurizing the autoclave, the isopropanol was removed from the reaction mixture at 100 mbar and 40° C. Subsequently, the residue was placed in a phase separator, allowing the separation of the catalyst and product phases. The product phase was analyzed by GC. The following composition was obtained (determined by GC):

| Ingredient (without solvent) | Surface % |
|---|---|
| head | 0.48 |
| DCP | 1.50 |
| TCD monoenal isomers | 3.38 |
| TCD dial isomers | 89.92 |
| TCD-OH | 2.20 |
| tail | 2.52 |

The results are obtained without considering the solvent content. The results show that almost 100% conversion was achieved with a very low catalyst concentration of 0.45 mol % based on the diolefin. Moreover, a TCD dial selectivity of about 90% was obtained.

Repeated conversion of DCPD to TCD was carried out with the addition of isopropanol in a single-phase region of the reaction solution. The experimental conditions were as follows in each case:

30 g DCPD per run 350 ppm $Rh(OAc)_2$ based on 300 g total mass

P/Rh ratio=10/1, corresponding to 18.38 g TPPTS in 135 g water 135 g isopropanol Reaction temperature: 130° C.

Reaction pressure: 50 bar

Response time: 3 h

The conversions and selectivities of the individual reactions corresponded to the results given above within the limits of error. After the end of the reaction at 100 mbar and 40° C., the isopropanol was removed from the reaction solution via a rotary evaporator and the residue was balanced. Then the remaining residue was transferred to a phase separator and phase separation was carried out at RT. The organic phase consisting of reaction products was removed, balanced and sampled for rhodium content and product fractions. The upper aqueous catalyst phase was also omitted, balanced and recombined with the previously removed isopropanol. Fresh DCPD was added to the combined catalyst phase and the mixture was again reacted in the reactor under 130° C. and 50 bar pressure synthesis gas for 3 h. The reaction was repeated five times iteratively. This procedure was iteratively repeated five times.

The individual weights of the organic phase over the 5 runs and their composition, in particular with regard to TCD dial and TCD monoenal, are constant. The proportion of rhodium in the organic phase is also constant and low. The amount of rhodium in the organic phase per run is about 3.2 ppm+−0.8 ppm % based on the total rhodium input. Thus, it could be shown that, in addition to a successful conversion of polycyclic diolefins which are difficult to hydroformylate, the process according to the invention also allows a very efficient and simple recovery and reuse of the catalyst.

FIG. 1 shows the result of the calculated phase behaviour of a three-component mixture as a function of the composition at a temperature of 120° C. The components are the aqueous solution of a Rh-TPPTS complex catalyst (bottom left), isopropanol as solvent (top) and the final product TCD dial (bottom right). The dashed region includes the mass fractions of the ternary compositions, which are two-phase at this temperature. In the non-dashed, upper region of the triangle, compositions are present which are single-phase under the pressure and temperature conditions. Since the solubilities of the olefin reactants are not significantly different from the solubilities of the intermediates and end products, this phase diagram is representative of the entire reaction with changing reactant/product ratios.

Further tests were carried out with other solvents and reactants. The test conditions for these tests are as follows:

| Components | Application quantities |
|---|---|
| Total rhodium concentration in aqueous catalyst solution in mg/L | 46380 |
| Amount of aqueous catalyst solution in mL | 4.20 |
| Rhodium in mmol | 1.89 |
| Ligand quantity in g | 35.68 |
| Ligand concentration in mmol/kg | 530 |
| P/Rh ratio | 10:1 |
| Olefin in % based on total input | 10 |
| Olefin in g | 50 |
| Olefin in mol | 0.378 |
| Rhodium quantity in % based on olefin | 0.5 |
| Quantity of isopropanol used in g | 225 |
| Quantity of water used in g | 225 |
| Synthesis gas composition H2:CO | 1:1 |

In deviation from the reaction conditions given above, n-propanol was used instead of isopropanol. Without optimizing the experimental conditions for the use of n-propanol, the reaction of dicyclopentadiene gives a TCD dial product fraction of 61.3% and an olefin conversion of 99.9%. This shows that the reaction can also be carried out in non-branched alcohols as solvents.

The reaction was repeated under the same process conditions as indicated above. In deviation, 20 g of methylcyclohexane (MCH) were additionally added as solvent. Without optimizing the experimental conditions for the use of this solvent mixture, the TCD dial product fraction is 69.15% and the olefin conversion is 99.5%. This shows that the reaction can also be carried out in solvent mixtures.

The reaction was repeated under the same process conditions as described above. In deviation from the reaction, 1-octene was now used as the olefin component instead of dicyclopentadiene. Without optimizing the experimental conditions to use a different olefin, the yield of the C9 aldehyde target components is 83.6% and the olefin conversion is 98%. This shows that the reaction can also be carried out with non-cyclic monoolefins.

The invention claimed is:

1. Process for the preparation of aldehydes by hydroformylation of olefins by means of synthesis gas over a transition metal complex catalyst, characterized in that within a first process step the olefins are reacted by means of an aqueous catalyst solution comprising a transition metal and ligands bonded thereto in the presence of a water-miscible solvent, the pressure, the temperature and the proportions of the solvent and the aqueous catalyst solution being controlled in such a way that the hydroformylation is carried out in a homogeneous single-phase reaction solution and within a second process step, by lowering the temperature and/or reducing the pressure, the homogeneous reaction solution obtained from the first reaction step is converted into a two-phase process solution and at least a part of the organic phase is separated from the aqueous phase; and, wherein further, the temperature and pressure are kept constant during the reaction and the single phase of the reaction solution is adjusted via the mass ratios of solvent to aqueous catalyst solution.

2. The process according to claim 1, wherein the first process step is performed at a pressure of greater than or equal to 0.5 MPa and less than or equal to 10 MPa and at a temperature of greater than or equal to 70° C. and less than or equal to 150° C.

3. The process according to claim 1, wherein the olefins have at least two non-conjugated double bonds.

4. The process according to claim 1, wherein the olefins comprise at least one aliphatic ring.

5. The process according to claim 1, wherein the molar ratio of water in the used aqueous catalyst solution to catalyst metal, expressed as moles of water divided by moles of catalyst metal, is greater than or equal to 5000 and less than or equal to 60000.

6. The process according to claim 1, wherein the metal of the aqueous catalyst solution is rhodium and the ligands comprise water-soluble diphosphines or triarylphosphines.

7. The process according to claim 1, wherein the mass ratio of aqueous catalyst solution to solvent, expressed as mass of catalyst solution divided by mass of solvent, is greater than or equal to 0.25 and less than or equal to 4.

8. The process according to claim 1, wherein the water-miscible solvent has a solubility in water at 20° C. of greater than or equal to 20 g/L.

9. The process according to claim 1, wherein the solvent is selected from the group consisting of straight or branched C2-C5 alcohols or mixtures of at least two alcohols from this group.

10. The process according to claim 1, wherein the solvent is isopropanol.

11. The process according to claim 1, wherein at least one ligand of the aqueous catalyst solution comprises a triphenylphosphine-3,3',3"-trisulfonic acid sodium salt.

12. The process according to claim 1, wherein the aqueous catalyst solution comprises triarylphosphine ligands and a catalyst metal, wherein the molar usage ratio of triarylphosphine ligands to catalyst metal, expressed as moles of triarylphosphine ligands divided by moles of catalyst metal, is greater than or equal to 3 and less than or equal to 15.

13. The process according to claim 1, wherein the molar ratio of catalyst metal to olefin, expressed as moles of catalyst metal divided by moles of olefin, is greater than or equal to 0.05% and less than or equal to 0.75%.

14. The process according to claim 1, wherein the pH of the aqueous catalyst solution is greater than or equal to pH 4 and less than or equal to pH 10.

* * * * *